United States Patent
Zambaux

(10) Patent No.: US 10,342,883 B2
(45) Date of Patent: *Jul. 9, 2019

(54) DISPOSABLE MEMBRANE

(71) Applicant: PALL LIFE SCIENCES BELGIUM, Hoegaarden (BE)

(72) Inventor: Jean-Pascal Zambaux, Audenge (FR)

(73) Assignee: PALL LIFE SCIENCES BELGIUM, Hoegaarden (BE)

( * ) Notice: Subject to any disclaimer, the term of this patent is extended or adjusted under 35 U.S.C. 154(b) by 420 days.

This patent is subject to a terminal disclaimer.

(21) Appl. No.: 14/665,835

(22) Filed: Mar. 23, 2015

(65) Prior Publication Data

US 2015/0258227 A1 Sep. 17, 2015

Related U.S. Application Data

(63) Continuation of application No. 13/322,054, filed as application No. PCT/EP2010/057293 on May 27, 2010, now Pat. No. 8,986,623.

(30) Foreign Application Priority Data

May 27, 2009 (EP) .................................... 09305483

(51) Int. Cl.
| | | |
|---|---|---|
| A61L 2/26 | (2006.01) |
| A61L 2/04 | (2006.01) |
| F26B 5/06 | (2006.01) |
| F26B 9/00 | (2006.01) |
| F26B 25/00 | (2006.01) |
| F26B 25/08 | (2006.01) |
| A61L 2/18 | (2006.01) |
| A61L 2/20 | (2006.01) |
| F27D 1/18 | (2006.01) |

(52) U.S. Cl.
CPC .................... *A61L 2/04* (2013.01); *A61L 2/18* (2013.01); *A61L 2/206* (2013.01); *A61L 2/208* (2013.01); *A61L 2/26* (2013.01); *F26B 5/06* (2013.01); *F26B 9/006* (2013.01); *F26B 25/008* (2013.01); *F26B 25/08* (2013.01); *F27D 1/18* (2013.01)

(58) Field of Classification Search
CPC ...................................... A61L 2/26; F26B 5/06
See application file for complete search history.

(56) References Cited

U.S. PATENT DOCUMENTS

| | | | | |
|---|---|---|---|---|
| 5,342,121 A * | 8/1994 | Koria | ........................ | B25J 21/02 312/1 |
| 7,174,772 B2 * | 2/2007 | Sacca | .................. | G01M 3/3218 73/49.2 |
| 8,986,623 B2 * | 3/2015 | Zambaux | .................. | A61L 2/26 34/523 |
| 2002/0179625 A1 * | 12/2002 | Huang | ............... | B65D 83/0805 221/63 |
| 2009/0014459 A1 * | 1/2009 | Hood | ................. | B65D 83/0805 221/45 |

* cited by examiner

*Primary Examiner* — Sean E Conley
(74) *Attorney, Agent, or Firm* — King & Schickli, PLLC

(57) ABSTRACT

The invention relates mainly to an apparatus comprising a chamber for physically and/or chemically treating one or more samples or products, said apparatus comprising a door for introducing samples inside the apparatus chamber or bringing samples outside the apparatus, said apparatus comprising a membrane or film defining a chamber wall inside said apparatus when the door is closed.

17 Claims, 3 Drawing Sheets

DISPOSABLE MEMBRANE

The invention relates mainly to an apparatus comprising a chamber for physically and/or chemically treating one or more samples or products, for example for temperature and/or pressure modification, and notably for sterilization, depyrogenation, or freeze-drying of samples. The invention relates further to a disposable membrane or film.

STATE OF THE ART

The prior art discloses many devices for sterilization, depyrogenation, or freeze-drying of samples. Once samples have been disinfected, sterilized or depyrogenated, they may be subjected to other operations. Typical operations are temperature and/or pressure modifications, such as freeze-drying.

However, when sterilized samples or products should be handled in another apparatus outside the disinfection, sterilization or depyrogenation devices the prior art discloses apparatus which force the operators to disinfect, sterilize or depyrogenate these other apparatus and manipulate samples via complex procedures. These procedures are costly and time consuming for the companies and especially for chemical or biochemical companies including pharmaceutical companies. For example, freeze-dryers are sterilized prior to any sterilized samples introduction, but samples should remain sterile up to the end of the manipulation. This is a technical problem.

One industrial solution is to surround the apparatus, such as a freeze-dryer, by an isolator so that the apparatus door is located inside said isolator. The whole isolator and apparatus are sterilized for example by a micro-fog or a bactericide gas. Accordingly when the door is open, the apparatus inner part is still under sterile atmosphere. However using this design forces the operator to use an isolator suit or cloth.

A second industrial way to manipulate samples especially after sterilization of such apparatus is to use conveyors for vials or containers to bring the vials or containers into the apparatus. However in case a vial or container is broken, a defined number of vials or container upstream and downstream should be disposed to avoid any contamination (cross-contamination). A laminar flow is used in front of the door of the apparatus (freeze-dryer) to introduce the samples into said apparatus under sterile atmosphere. In this case the operator should himself (herself) sterilize the door and apparatus outer part. Alcohol is often used for this operation, but the door mechanical parts (such as jack, screws, handle, etc) are not sterilizable or very difficult to sterilize.

Accordingly the prior art is faced with many technical problems due to these operations, in particular when high quality chemical, biochemical, or pharmaceutical samples are to be introduced in an apparatus such as a freeze-dryer, or the like.

GOAL OF THE INVENTION

The prior art does not respond to need from the chemical/pharmaceutical/medical industry.

The present invention aims to solve the technical problem of providing a device or apparatus which may be easily disinfected, sterilized and/or freed from pyrogen (or depyrogenated) and wherein such a state may be kept and/or controlled easily. This apparatus is typically an oven, a drying equipment, a dryer, a freeze-dryer, an autoclave, a sterilizer, a gas chamber, or a depyrogenation apparatus.

Accordingly, the invention aims to provide such a device for the chemical, the food, the pharmaceutical, and/or the medical industry.

The invention aims to solve the new technical problem of providing a ready-to-use or disposable equipment for the above mentioned apparatus or operations.

DESCRIPTION OF THE INVENTION

The present invention relates to an apparatus comprising a chamber for physically and/or chemically treating one or more samples or products, for example by temperature and/or pressure modification, said apparatus comprising a door for introducing samples inside the apparatus chamber or bringing samples outside the apparatus, said apparatus comprising a membrane or film defining a chamber wall inside said apparatus when the door is closed.

The film or membrane advantageously separates the apparatus chamber from the apparatus outside when the door is open, so that when said apparatus chamber is sterile, disinfected, or freed from pyrogen, said chamber remains sterile, disinfected, or freed from pyrogen when the door is open.

According to one embodiment, the membrane or film comprises a joint or seal for sealing the membrane or film along the apparatus inside periphery.

Advantageously, the apparatus comprises a channel along the transversal section inside periphery and wherein said joint or seal is inserted into said channel to isolate, by said membrane or film, the chamber from the outside atmosphere when the door is open. "Isolate" means at least keeping the chamber disinfected, sterile or depyrogenated. Said channel may be part of a supplementary apparatus piece complementary to the apparatus inside periphery. This frame may be positioned in the apparatus chamber, and preferably near the door of said apparatus to get the maximum volume of apparatus chamber. Such a supplementary piece may be referred to as a frame. This frame may comprise advantageously one or more means for locking said frame to the apparatus inside periphery, such as weldings to fix the frame to the apparatus and to ensure a good watertightness between the frame and the apparatus.

Advantageously, said joint or seal is inserted within the membrane or film, such as in a fold.

In one embodiment, the membrane or film is made of a material selected from the group consisting of a polymer selected from the group of a thermoplastic, a polyethylene (PE), a polypropylene (PP), a polyaryletherketone, a PEEK (Poly(ether ether ketone), in particular poly(oxy-1,4-phenylene-oxy-1,4-phenylene-carbonyl-1,4-phenylene); a polytetrafluoroethylene (PTFE); a perfluoroalkoxy (PFA) polymer; a poly(tetrafluoroethylene-co-perfluoromethyl vinyl ether) (MFA); a polyperfluoro(ethylene-co-propylene) (FEP); a poly(ethylene-alt-chlorotrifluoroethylene) (ECTFE); a poly(ethylene-co-tetrafluoroethylene) (ETFE); a poly(vinylidene fluoride) (PDVF); a tetrafluoroethylene-co-hexafluoropropylene-co-vinylidene fluoride terpolymer (THV); a poly(bisphenol A-co-4-nitrophthalic anhydride-co-1,3-phenylenediamine) (PEI); a poly(4-methyl-1-pentene) (PMP); and suitable mixtures thereof.

The apparatus is advantageously selected from the group consisting of an oven, a drying equipment, a dryer, a freeze-dryer, an autoclave, a sterilizer, a gas chamber (for example for cold gas sterilization such as $H_2O_2$ or ethylene oxide sterilization), and a depyrogenation apparatus.

The membrane or film advantageously comprises an inlet and an outlet for vials or containers for locating one or more vials or containers inside said chamber or discharging these vials or containers.

In one embodiment the membrane or film comprises a proximal end and a distal end, said proximal end comprising an inlet comprising an inlet port for introducing one or more vials or containers inside said chamber through said port, and/or an outlet comprising an outlet port for removing one or more vials or containers from said chamber through said port, said distal end defining a section essentially complementary to the apparatus transversal section inside periphery, said membrane or film comprising a fold in which an inflatable seal is inserted, said fold being inserted in a channel extending along the apparatus transversal section inside periphery to isolate the chamber inner part from the chamber outer part.

In a particular embodiment the closing means are placed around the outlet and/or inlet to close the outlet port and/or inlet port for example by compression or squeezing to isolate said chamber from the outside atmosphere, and wherein said outlet and/or inlet port closing means in open position allow the passage of one or more vials or containers. Said closing means may be or comprise one or more doors, gates, valves, clamps, screws, nuts, bolts, weldings, or zips.

The film or membrane may comprise one or more gloves for manipulating vials or containers inside said chamber.

The invention further relates to a method for subjecting samples to a physical and/or chemical treatment, for example to a temperature and/or pressure modification, in an apparatus comprising a chamber for a physical and/or chemical treatment, for example for temperature and/or pressure modification, said apparatus comprising a door for introducing samples inside the apparatus chamber or bringing samples outside the apparatus, said apparatus comprising a membrane or film defining a chamber wall inside said apparatus when the door is closed, said apparatus being notably defined according to the above and below description, wherein said method comprises:
  (i) opening said apparatus door;
  (ii) introducing said samples into said apparatus chamber;
  (iii) closing said apparatus door;
  (iv) physically and/or chemically treating said samples into said apparatus chamber, for example by modifying the temperature and/or pressure of said chamber;
  (v) opening said apparatus door; and
  (vi) removing said samples from the apparatus chamber.

In one embodiment, the sample are introduced into and/or removed from said apparatus chamber via an inlet and/or outlet located on said membrane or film.

According to the invention, products or samples may be manipulated without any contact with the atmosphere outside the chamber. The chamber may be disinfected, sterilized and/or depyrogenated in order to manipulate products or samples that require such operating conditions. Such products or samples may be chemical or biochemical products such as pharmaceutical, cosmetic, food, or medical products or samples.

Products or samples may be advantageously freeze-dried using the apparatus of the present invention. Thus the invention relates notably to a freeze-drying method.

The apparatus of the present invention allows to put disinfected, sterilized or depyrogenated products inside the chamber via an inlet of the film or membrane, then close this inlet by a closing means, for example by one or more clamps, screws, nuts, bolts, weldings, zips, doors, gates, or valves, which may be automated and/or computer-controlled. The whole film or membrane is then put inside the apparatus if a membrane or film part (such as a proximal end, an inlet and/or an outlet) was extending outside the apparatus, and the door of the apparatus is closed. The products may be subjected to the operating steps performed by said apparatus (autoclave, freeze-dryer, oven, etc) such as heating, pressurising, freeze-drying, etc. Than the products may be discharged either via the inlet or another outlet of the film or membrane after the closing means is opened. The inlet and/or the outlet should be advantageously connected to a disinfected, sterilized and/or depyrogenated device before the samples or products are introduced or brought outside said apparatus chamber. Such a device may be for example the device disclosed in the French patent application no. FR 08 54131 to CHANGEXPLORER and/or in the European patent application no. EP 09305210.8 to DISPOSABLE LAB, both incorporated by reference. Such devices may be connected via one or more clamps and/or screws. Vials or containers may be filled by products in a device disclosed in no. EP 09305210.8 according to the procedure described. The transfer between this device and the apparatus of the present invention may be performed using a device described in FR 08 54131.

Once the samples are physically and/or chemically treated in said apparatus, the film or membrane may be disposed and optionally replaced by a new one.

The invention further relates to a film or membrane made of a polymer material which do not degrade under operating conditions, such as under freeze-drying conditions, said membrane or film comprising a fold surrounding an inflatable joint or seal, said film or membrane comprising an inlet comprising an inlet port, and/or outlet means comprising an outlet port, for allowing the passage of one or more vials or containers, said inlet and outlet means comprising a closing means to close the inlet and/or the outlet port.

The film or membrane may comprise gloves, preferably made of the same polymer material, for manipulating said vials or containers.

The film or membrane may advantageously comprise a proximal end and a distal end, said proximal end comprising an inlet comprising an inlet port for allowing the passage of one or more vials or containers through said port, and/or an outlet comprising an outlet port for allowing the passage of one or more vials or containers through said port, said distal end defining a rectangular shape, said distal end of said membrane or film comprising a fold along the rectangular shape periphery in which a seal, preferably an inflatable seal, is inserted.

The invention further relates to a chamber frame for an apparatus comprising a chamber for physically and/or chemically treating samples or products, and in particular a chamber for temperature and/or pressure modification, said chamber frame comprising a channel for receiving said membrane or film.

In one embodiment, the channel is extending along the transversal section inside periphery of said frame.

"Traversal section inside periphery" means the inside periphery of the transversal section.

Said chamber frame may be marketed including the film or membrane of the invention. In such a case the inflatable joint or seal of the film or membrane may be inflated in situ to fix or fit the film or membrane to or into the frame channel.

Embodiments and particular aspects of the invention may be combined together.

Other aims, characteristics and advantages of the invention will appear clearly to the person skilled in the art upon reading the explanatory description which makes reference to the figures which are given simply as an illustration and which in no way limit the scope of the invention.

The figures make up an integral part of the present invention, and any characteristic which appears novel with respect to any prior state of the art from the description taken in its entirety, including the figures, makes up an integral part of the invention in its function and in its generality.

Thus, every figure has a general scope.

Figure 1A:
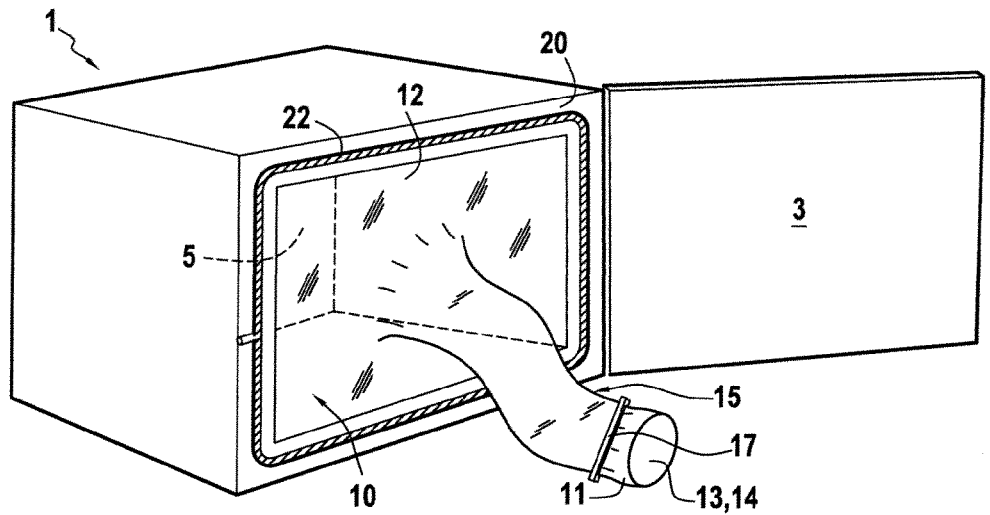
FIGS. 1A and 1B represent a perspective view of an embodiment of an apparatus according to the present invention.
Figure 4:
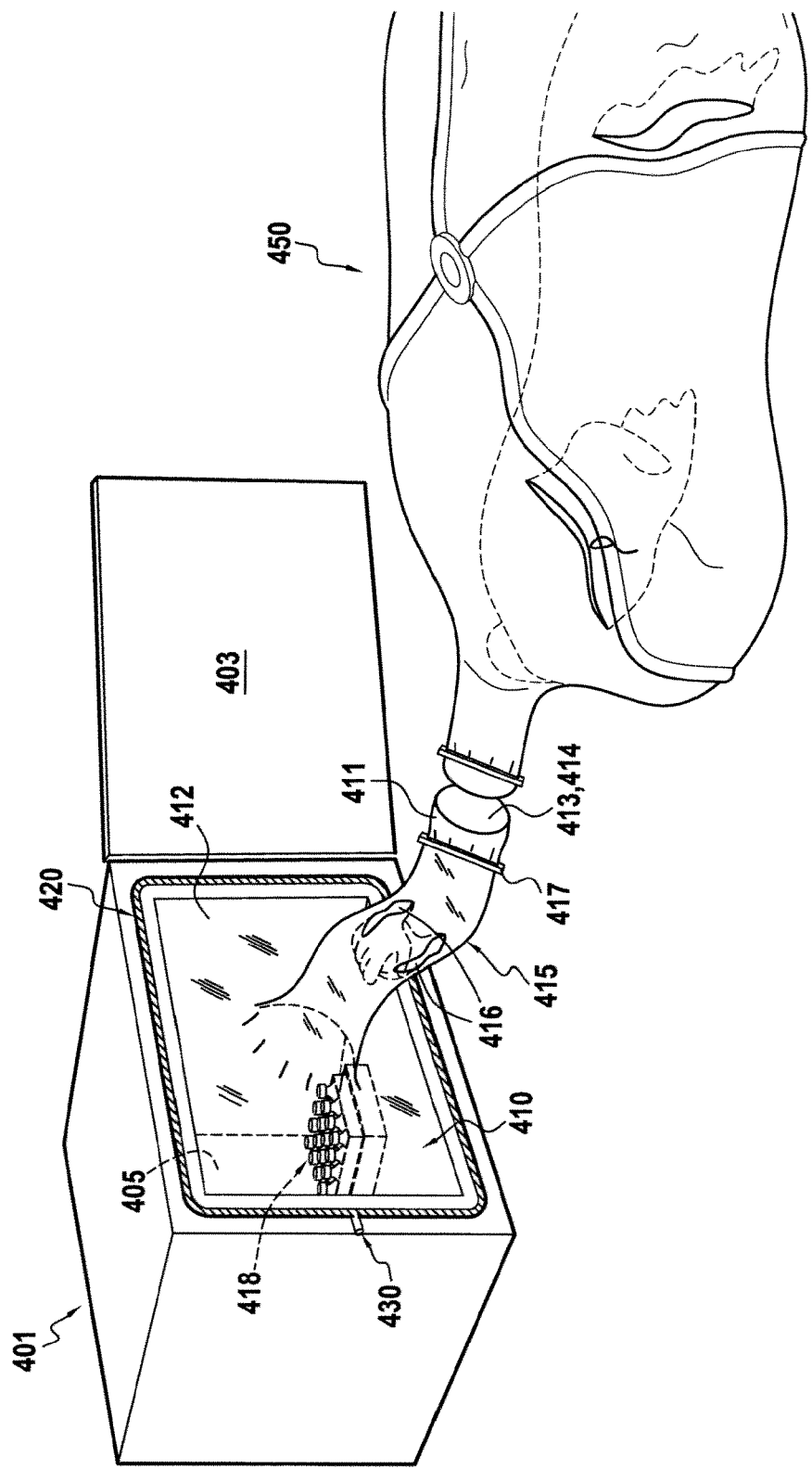
FIG. 4 represents a scheme of a use of an apparatus of the present invention.
Figure 5:
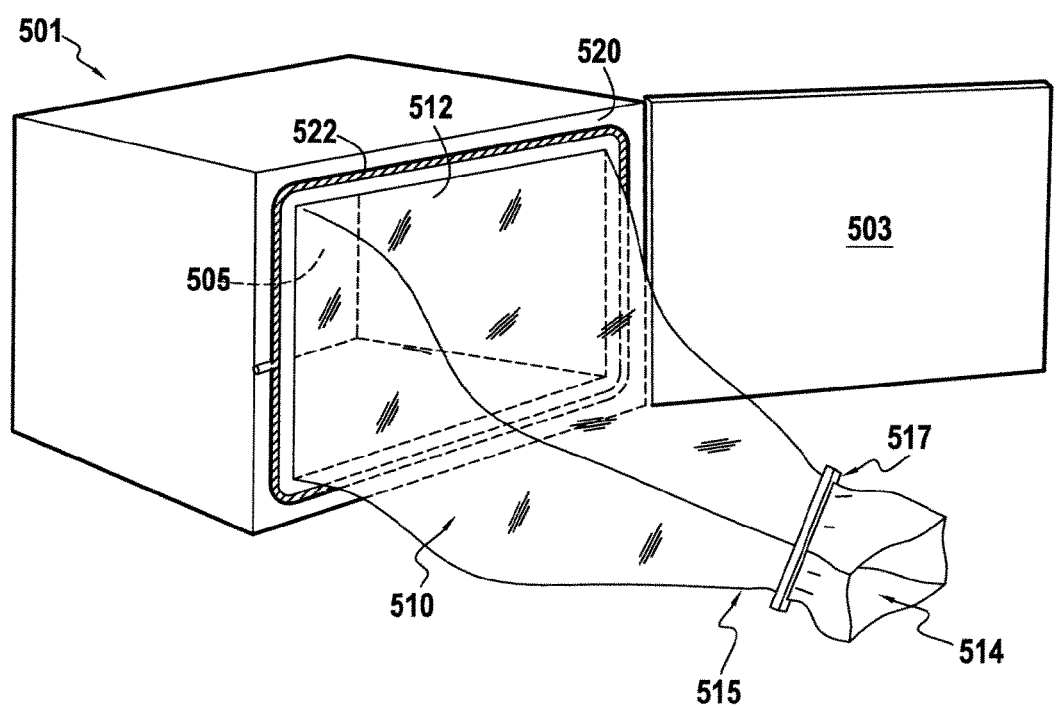
FIG. 5 represents a perspective view of an embodiment of an apparatus according to the present invention.

FIGS. 1A, 4, and 5 represent an embodiment of an apparatus (1, 401, 501) according to the present invention. The apparatus (1, 401, 501) comprises a chamber (5, 405, 505) for temperature and/or pressure modification, said apparatus (1, 401, 501) comprising a door (3, 403, 503) for introducing samples inside the apparatus chamber (5, 405, 505) or bringing samples outside the apparatus (1, 401, 501), said apparatus (1, 401, 501) comprising a membrane (10, 410, 510) or film (10, 410, 510) defining a chamber (5, 405, 505) wall inside said apparatus (1, 401, 501) when the door (3, 403, 503) is closed. The membrane or film (10, 410, 510) comprises a proximal end (11, 411, 511) and a distal end (12, 412), said proximal end (11, 411, 511) comprising an inlet (13, 413, 513) comprising an inlet port for introducing one or more vials or containers (418) inside said chamber (5, 405, 505) through said port, and/or an outlet (14, 414, 514) comprising an outlet port for removing one or more vials or containers (418, 518) from said chamber (5, 405, 505) through said port, said distal end (12, 412, 512) defining a section essentially complementary to the apparatus, or frame, transversal section inside periphery, said distal end (12, 412, 512) of said membrane or film (10, 410, 510) comprising a fold in which an inflatable seal (22, 522) is inserted (see FIGS. 2A and 2B), said fold being inserted in a channel (21) extending along the apparatus (1, 401, 501) transversal section inside periphery to isolate the chamber (5, 405, 505) inner part from the chamber (5, 405, 505) outer part. Such a fold may be thermosealed. Said fold may be inserted in a channel (21) extending along a frame (20, 420, 520) transversal section inside periphery, wherein said frame is inserted into said apparatus. This allows adapting more easily the frame to any marketed apparatus.

Figure 2A:
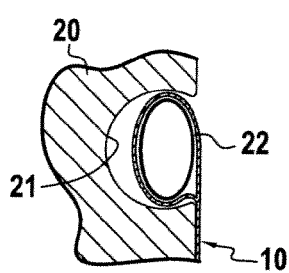
FIGS. 2A and 2B represent a section of an embodiment of the film or membrane according to the present invention.
Figure 2B:
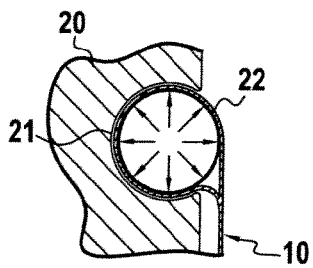

FIGS. 2A and 2B show a section of an inflatable seal inserted in a channel (21) extending along a frame (20). FIG. 2A shows in particular the non-inflated seal (22) and FIG. 2B shows the inflatable seal (22) inflated into said channel (21).

As illustrated in FIGS. 1A, 1B, 4 and 5, the inlet and outlet may be located at the same place, but they may be separately located.

Figure 1B:
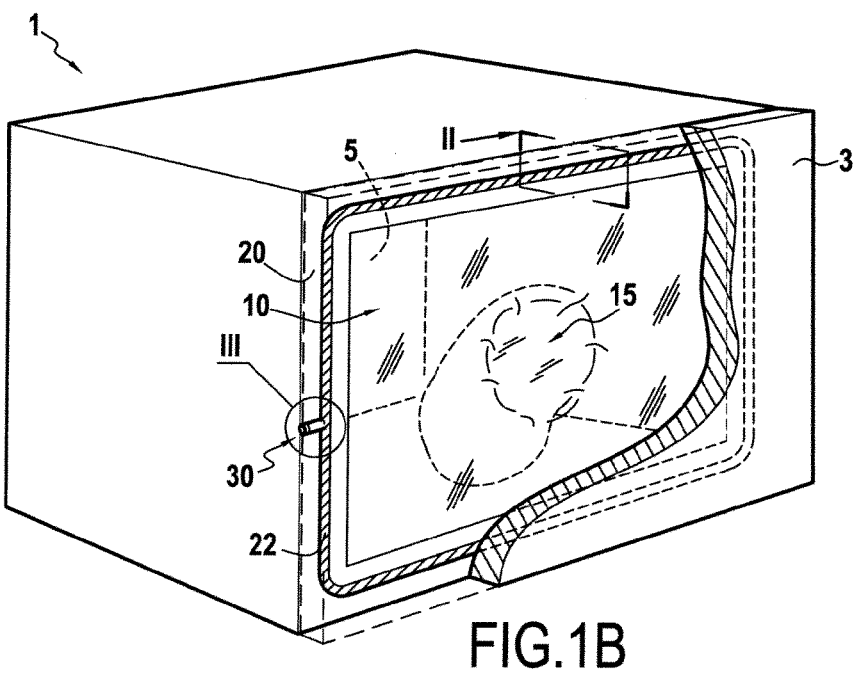

No particular shape is given to the proximal end. As illustrated on FIGS. 1A and 1B, the proximal end has a cylindrical shape. In a particular industrial embodiment, said proximal end has a rectangular section, such as illustrated in FIG. 5. Advantageously, said shape is designed to allow easy manipulations of vials or containers via said inlet and/or outlet. The manipulation, i.e. the introduction through the inlet and/or the removal through the outlet may be automated and/or computer-controlled. In particular samples or products may be put in the apparatus via a conveyor, for example by a belt conveyor. FIG. 1B shows that the membrane or film (10, 410, 510) or the proximal end (15, 415, 515) thereof, may be folded back into the chamber (5, 405, 505) or between the chamber (5, 405, 505) and the door (3, 403, 503), when the door is open.

Figure 3:
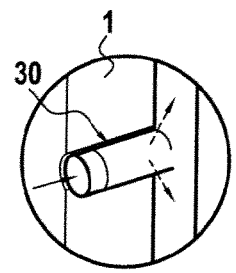
FIG. 3 represents a schematic view of a tube insert for an inflatable seal of the present invention.

FIG. 3 represents an inflatable seal part (30) comprising a tube for allowing the inflation of the seal (22). Such a tube may be radially positioned on a cylindrical seal (22). The film or membrane (10, 410, 510) may comprise a hole for allowing the passage of said tube. Further it is preferred that said film or membrane (10, 410, 510) hole periphery is thermosealed or fixed by any other means to the tube so that chamber (5, 405, 505) remains disinfected, sterile or depyrogenated. Conventional devices are available to inflate seals.

The apparatus may comprise one or more means for maintaining a small overpressure (for example an overpressure of 1 to 100 kPa) in the chamber (5). Such an overpressure may be maintained via perforations in the inflatable seal (22) and frame (20), said perforations facing the chamber (5).

The invention claimed is:

1. An apparatus comprising:
   a disinfector including a chamber for receiving one or more samples or products and a door adapted for moving between a closed position and an open position for introducing the one or more samples or products inside the chamber or bringing the one or more samples or products outside the chamber;
   a membrane or film for isolating the chamber from the outside atmosphere, said membrane or film defining a chamber wall inside said apparatus when the door is in the closed position, said membrane or film including a sealable passage for passing the one or more samples or products through the membrane or film into the chamber.

2. The apparatus of claim 1, wherein said membrane or film comprises a joint or seal for sealing the membrane or film along a periphery of the chamber.

3. The apparatus of claim 2, further comprising a channel along the periphery for receiving the joint or seal.

4. The apparatus of claim 2, wherein said joint or seal is inserted within a fold of the membrane or film.

5. The apparatus of claim 1, wherein said membrane or film is made of a material selected from the group consisting of a polymer selected from the group of a thermoplastic, a polyethylene (PE), a polypropylene (PP), a polyaryletherketone, a PEEK (Poly(ether ether ketone), in particular poly(oxy-1,4-phenylene-oxy-1,4-phenylene-carbonyl-1,4-phenylene); a polytetrafluoroethylene (PTFE); a perfluoroalkoxy (PFA) polymer; a poly(tetrafluoroethylene-co-perfluoromethyl vinyl ether) (MFA); a polyperfluoro(ethylene-co-propylene) (FEP); a poly(ethylene-alt-chlorotrifluoroethylene) (ECTFE); a poly(ethylene-co-tetrafluoroethylene) (ETFE); a poly(vinylidene fluoride) (PDVF); a tetrafluoroethylene-co-hexafluoropropylene-co-vinylidene fluoride terpolymer (THV); a poly(bisphenol A-co-4-nitrophthalic anhydride-co-1,3-phenylenediamine) (PEI); a poly(4-methyl-1-pentene) (PMP); and suitable mixtures thereof.

6. The apparatus of claim 1, wherein said membrane or film comprises a proximal end and a distal end, said proximal end comprising an inlet to the passage and said distal end defining a section essentially complementary to a periphery of said chamber, said distal end of said membrane or film comprising a fold in which an inflatable seal is inserted, said fold being inserted in a channel extending along the periphery of the chamber to isolate a chamber inner part from a chamber outer part.

7. The apparatus of claim 1, wherein a closure is provided for closing the passage through the membrane or film into the chamber, and wherein said closure in an open position allows the passage of the one or more samples or products.

8. The apparatus of claim 1, wherein said film or membrane comprises one or more gloves for manipulating the one or more samples or products inside said chamber.

9. The apparatus of claim 1, wherein the disinfector is selected from the group consisting of an oven, a drying equipment, a dryer, a freeze-dryer, an autoclave, a sterilizer, a gas chamber, and a depyrogenation apparatus.

10. The apparatus of claim 1, wherein the disinfector comprises an oven.

11. An apparatus comprising:
a housing including a chamber for receiving one or more samples or products, said chamber surrounded by a periphery; and
a membrane or film forming a chamber wall inside said housing for isolating the chamber from the outside atmosphere, said membrane or film further comprising a joint or seal for sealing the membrane or film about the periphery of the chamber and a sealable passage for passing the one or more samples or products though the membrane or film into the chamber.

12. The apparatus of claim 11, wherein the housing forms part of a device selected from the group consisting of an oven, a drying equipment, a dryer, a freeze-dryer, an autoclave, a sterilizer, a gas chamber, and a depyrogenation apparatus.

13. The apparatus of claim 11, wherein the passage comprises a tubular structure formed by the film or membrane and extending in a direction opposite the chamber for passing the one or more samples of products to or from the chamber, and further including a closure external to the chamber for closing the passage.

14. The apparatus of claim 11, wherein the housing includes a door adapted for being opened and closed, and wherein at least part of the membrane or film is sandwiched between the door and the periphery of the chamber when the door is closed.

15. An apparatus comprising:
an oven including a chamber for receiving one or more samples or products, said chamber surrounded by a periphery; and
a membrane or film forming a chamber wall inside said housing for isolating the chamber from the outside atmosphere, said membrane or film further comprising a joint or seal for sealing the membrane or film about the periphery of the chamber and a sealable passage for passing the one or more samples or products though the membrane or film into the chamber.

16. The apparatus of claim 11, wherein said film or membrane comprises gloves for manipulating the one or more samples or products inside said chamber.

17. The apparatus of claim 11, wherein a periphery of the sealable passage corresponds to the periphery surrounding the chamber.

* * * * *